United States Patent [19]

Takayanagi et al.

[11] Patent Number: 4,750,910

[45] Date of Patent: Jun. 14, 1988

[54] INDIGO BLUE-COLORED BIOABSORBABLE SURGICAL FIBERS AND PRODUCTION PROCESS THEREOF

[75] Inventors: Hiroshi Takayanagi; Tadashi Kobayashi; Eiji Senoue; Masao Imai, all of Ohmuta, Japan

[73] Assignee: Mitsui Toatsu Chemicals, Incorporated, Tokyo, Japan

[21] Appl. No.: 4,708

[22] Filed: Jan. 20, 1987

[30] Foreign Application Priority Data

Jan. 22, 1986 [JP] Japan ................................ 61-009951
Dec. 5, 1986 [JP] Japan ................................ 61-288890

[51] Int. Cl.$^4$ .......................... C09B 7/00; C09B 67/00; A61L 17/00
[52] U.S. Cl. .......................................... 8/563; 8/489; 8/497; 8/653; 8/916; 128/335.5; 264/78; 264/210.6; 264/211; 528/354
[58] Field of Search ...................... 8/653; 128/335.5; 8/563, 653

[56] References Cited

U.S. PATENT DOCUMENTS

| | | | |
|---|---|---|---|
| 3,034,850 | 5/1962 | King | 8/563 |
| 3,047,352 | 7/1962 | Santoro et al. | 8/653 |
| 3,297,033 | 1/1967 | Schmitt et al. | 128/335.5 |
| 3,527,556 | 9/1970 | Riley | 8/504 |
| 3,636,956 | 1/1972 | Schneider | 128/335.5 |
| 3,839,297 | 10/1974 | Wasserman et al. | 128/335.5 |
| 4,008,303 | 2/1977 | Glick et al. | 264/78 |

FOREIGN PATENT DOCUMENTS

| | | |
|---|---|---|
| 988939 | 4/1965 | United Kingdom . |
| 1098917 | 1/1968 | United Kingdom . |
| 1123445 | 8/1968 | United Kingdom . |
| 1375008 | 11/1974 | United Kingdom . |

OTHER PUBLICATIONS

Pharmaceutical News Index, file 42, & Medical Devices, Diagnostics and Instrumentation Reports–(The Gray Sheet), vol. 10, No. 31 Jul. 30, 1984.
Chemical Abstracts, vol. 101, No. 14, Oct. 1, 1984, pp. 344, abstract No. 116623p, Columbus, Ohio.

*Primary Examiner*—A. Lionel Clingman
*Attorney, Agent, or Firm*—Oblon, Fisher, Spivak, McClelland & Maier

[57] ABSTRACT

Blue-colored bioabsorbable surgical fibers are obtained by adding and dispersing a bioabsorbable polymer, which is selected from polyglycolic acid, poly(l-lactic acid) and glycolic acid-l-lactic acid copolymers all of which are useful as surgical fibers, and indigo in a nonaqueous organic solvent having low solubility for the polymer and indigo, heating the resultant dispersion at a temperature below 120° C. to distill off the solvent, thereby to obtain a master batch with the indigo incorporated therein at a high concentration, mixing and kneading the master batch with a fresh supply of the polymer, and then spinning the resultant polymer mixture.

2 Claims, No Drawings

INDIGO BLUE-COLORED BIOABSORBABLE SURGICAL FIBERS AND PRODUCTION PROCESS THEREOF

BACKGROUND OF THE INVENTION (1) Field of the Invention:

This invention relates to surgical fibers, such as sutures, obtained from polyglycolic acid, poly(l-lactic acid) or a glycolic acid-l-lactic acid copolymer, specifically, to blue-colored bioabsorbable surgical fibers obtained from the above polymer and to a production process thereof.

(2) Description of the Invention:

Polyglycolic acid, poly(l-lactic acid) and their copolymers are solid and have high bioabsorbability and hydrolyzability. Those having high polymerization degrees are spun or braided or processed into non-woven fabric and are hence used as surgical materials such as surgical sutures and gauze.

These bioabsorbable high-molecular materials have grayish yellow colors or substantially translucent gray colors, for example, when they are spun for use as sutures. When they are used as sutures in surgery, they are therefore stained in a red color with blood so that the stitched parts are hardly distinguishable and their distinction often presents difficulties during the surgery.

In order to solve such a problem, there have been known those colored with desired various pigments so as to permit their distinction at first glance even after stained with blood, in the case of sutures made of materials other than bioabsorbable high-molecular materials, for example, nylons, polyesters and the like. Such pigment-dependent coloring did not cause any problem in the case of sutures made of materials to be taken out after completion of suture, like aforementioned nylons and polyesters.

However, sutures made of bioabsorbable high-molecular materials are not taken out owing to their advantage even after completion of suture of surgical sites. A coloring agent which is employed to color sutures made of such a bioabsorbable high-molecular material is supposed to be non-toxic to human bodies and at the same time to be promptly absorbed and excreted. As a corollary, a limitation is naturally imposed on usable coloring agents.

Under the above-described circumstances, United States Food and Drug Administration has established a guideline as to the coloring of surgical sutures made of bioabsorbable high-molecular materials that they may be colored with coloring agents authorized as non-toxic by the Administration. Various specifications and standards have also been established with respect to tar dyes for foods, drugs and cosmetics in Japan. Tar dyes usable in drugs and quasi-drugs for external use are listed up ("Manual of Dyes", pp 222–223).

Among such dyes, certain oil-soluble dyes have already been known to be useful for coloring bioabsorbable sutures and the like. In U.S. Pat. No. 4,008,303, 1,4-bis(p-toluidino)anthraquinone (C.I. Solvent Green 3) is used as a coloring agent suitable for use in coloring polyglycolic acid. U.S. Pat. No. 3,839,297 discloses the use of 1-hydroxy-4-p-toluidinoanthraquinone (C.I. Solvent Violet 13) as a coloring agent for sutures made of glycolic acid-lactic acid copolymers.

These coloring agents are however oil-soluble ones which are employed usually as colorants for resins. When employed directly in human bodies, they are not absolutely considered to be non-toxic. Further, the coloring agent disclosed in U.S. Pat. No. 4,008,303 is a green one. Sutures colored by this coloring agent are therefore turned into a black color upon adhesion of blood, thereby making it difficult to distinguish them. On the other hand, the coloring agent described in U.S. Pat. No. 3,839,297 is a purple dye. Vividly-colored bioabsorbable high-molecular materials cannot be obtained unless their coloring with the coloring agent is effected by adding the coloring agent in the course of the polymerization of the materials. It has however been found that the coloring agent is caused to evaporate to a considerable extent during the polymerization and its loss is unignorably substantial.

As has been described above, none of such conventionally-known coloring agents are satisfactory as coloring agents for bioabsorbable high-molecular materials.

SUMMARY OF THE INVENTION

An object of this invention is to provide bioabsorbable surgical fibers which are free of the above-described problems of the prior art and are colored with a coloring agent safe for living bodies and distinguishable readily during surgery when the fibers are formed as sutures as well as a production process thereof.

With the aforementioned problems in view, the present inventors have carried out an investigation in order to develop a bioabsorbable high-molecular material colored with a safer and readily-distinguishable color.

As a result, it has now been found that a bioabsorbable high-molecular material colored in a vivid blue color can be obtained by using indigo, which has conventionally been employed for coloring cellulose fibers and is used only in the form of an aqueous solution upon coloring them, for the coloration of the bioabsorbable high-molecular material, leading to completion of this invention.

Indigo has been known as a vat dye (C.I. Vat Blue 1) for many years and is a component of natural indigo. It has the following advantages. Namely, it is one of tar dyes usable in surgical drugs and is absolutely non-toxic to human bodies. Moreover, materials colored with indigo are blue and upon adhesion of blood, their colors are changed to purple so that the materials are readily distinguishable.

Bioabsorbable high-molecular materials making use of indigo have however been unknown to date in spite of the aforementioned advantages, probably, for the following reason.

Namely, indigo is a vat dye and is hence used as an aqueous solution upon dyeing cellulose fibers. On the other hand, it is known that bioabsorbable polymers such as polyglycolic acid and polylactic acid are hydrolyzed and their strengths are thus reduced when water is present even in a small amount. For this reason, indigo has been believed to be absolutely inappropriate for coloring these bioabsorbable polymers.

Pellets of a bioabsorbable polymer, which were colored in a vivid blue color, were however obtained in accordance with the process of this invention, namely, when the bioabsorbable polymer and indigo were dispersed in a non-aqueous organic solvent having low solubility for the bioabsorbable polymer to prepare a master batch and the master batch was kneaded with a fresh supply of the bioabsorbable polymer. According to the above process, indigo surprisingly exhibits superb tinting power for bioabsorbable polymers such as polyglycolic acid and polylactic acid although indigo is a vat dye.

In one aspect of this invention, there is thus provided blue-colored bioabsorbable surgical fibers made of a polymer obtained by coloring a bioabsorbable polymer, which is selected from polyglycolic acid, poly(l-lactic acid) and glycolic acid-l-lactic acid copolymers all of which are useful as surgical fibers, with indigo into a blue color.

In another aspect of this invention, there is also provided a process for the production of blue-colored bioabsorbable surgical fibers, which comprises adding and dispersing a bioabsorbable polymer, which is selected from polyglycolic acid, poly(l-lactic acid) and glycolic acid-l-lactic acid copolymers all of which are useful as surgical fibers, and indigo in a non-aqueous organic solvent having low solubility for the polymer and indigo, heating the resultant dispersion at a temperature below 120° C. to distill off the solvent, thereby to obtain a master batch with the indigo incorporated therein at a high concentration, mixing and kneading the master batch with a fresh supply of the polymer, and then spinning the resultant polymer mixture.

DETAILED DESCRIPTION OF THE INVENTION AND PREFERRED EMBODIMENTS

Bioabsorbable polymers useful for spinning in the present invention are polyglycolic acid, poly(l-lactic acid) and glycolic acid-l-lactic acid copolymers.

Preferably, the above polymers which are employed in the present invention have the following physical properties. These polymers are still usable even if they contain copolymerized components and/or additives, so long as their physical properties fall within the following ranges respectively.

The intrinsic viscosities ($[\eta]$) and melt indexes (MI) of these polymers were measured in the following manner.

Intrinsic viscosities ($[\eta]$)

Each sample polymer was dissolved in a mixed solvent of phenol (10 parts by weight) and trichlorophenol (7 parts by weight). Its intrinsic viscosity was measured at 30±0.1° C. and a concentration of 0.5% by means of an Ubbelohde's viscometer.

Melt indexes (MI)

Each sample polymer was extruded in accordance with the method prescribed in ASTM D1238-65T published by American Society for Testing Materials, namely, 325 g of the sample polymer was extruded at 230° C. through an orifice of 2.1 mm wide and its MI was indicated in terms of the number of grams passed through the orifice per 10 minutes.

Polyglycolic acid $[\eta] = 0.8-1.3$ $MI = 0.1-5.0$

Poly(l-lactic acid)

$[\eta] = 1.0-2.0$ $MI = 0.1-5.0$

Glycolic acid-l-lactic acid copolymers $[\eta] = 1.0-2.0$ $MI = 0.1-5.0$

Bioabsorbable polymers having these physical properties can be obtained by a method known per se in the art. Those obtained in the following manner are however preferred.

Glycolide or l-lactide is charged in a polymerization vessel. After addition of stannous octate in an amount less than that employed routinely (in usual processes, stannous octate is used in an amount of about 0.03% or so based on the glycolide or l-lactide), namely, in an amount of about 0.003 wt. % as a solution in a solvent like chloroform and a linear aliphatic alcohol such as lauryl alcohol in an amount greater than that employed usually (in usual processes, such a linear aliphatic alcohol is used in an amount of about 0.06% based on stannous octate), namely, in an amount of about 0.3 wt. %, the resultant mixture is deaerated in vacuo. The polymerization vessel is then purged with nitrogen or argon and in a nitrogen or argon atmosphere, the mixture is heated to a temperature slightly higher than that employed in usual processes, namely, to about 200° C. in the case of polymerization of l-lactide and to about 230° C. in the case of polymerization of glycolide, at which the polymerization is effected for 2–6 hours. After completion of the polymerization, the resultant polymer is drawn out of the vessel from a lower part thereof and is then delivered to a pelletizer in order to pelletize same.

The thus-obtained polymer has an extremely low tin content and moreover, its molecular weight falls within a range of about 10,000 to about 100,000. When it is measured under the above-described conditions, the intrinsic viscosity is 0.8 or higher in the case of polyglycolic acid and at least 1.0 in the case of polylactic acid. It is hence possible to obtain a polymer suitable for use as a bioabsorbable polymer in the production of surgical sutures and the like. When their copolymers are desired, their copolymers having the above-described physical properties can be obtained in a manner similar to the above-described procedure.

In the present invention, it is preferable to pelletize the thus-obtained bioabsorbable polymer into granules or particles the sizes of which are not greater than 3 mm, followed by their coloring. Any granule sizes greater than 5 mm are not preferred because irregular coloring occurs when spun after coloring.

As a method for coloring the polymer with indigo, the following procedure can be followed in the present invention.

Commercially-available indigo powder having an average particle size of 5 μm or smaller can be used as is. In the case of a commercial product with a water dispersant mixed therein, it is recommended to use it after removing the dispersant completely by washing it with hot water and then drying same. After such a treatment, the commercial product is ready for use. Even in the case of purified indigo which is not supposed to contain any substance other than indigo, it seems to contain impurities byproduced upon production of indigo, such as indirubin

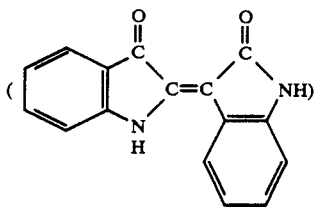

and indoxyl red

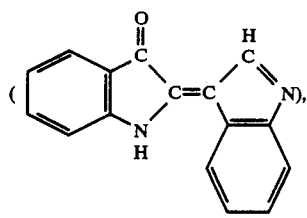

albleit in trace amounts. These impurities are oil-soluble and cannot be eliminated by any usual purification methods for indigo. Dyed polymers containing these impurities have somewhat inferior quality and present blue colors tinged slightly brownish.

In order to obtain fibers having higher quality and a vivid blue color, it is therefore preferable to remove the above-described byproducts from indigo to be used. Namely, indigo to be used is washed and purified with concentrated hydrochloric acid in advance.

Specifically, indigo powder commonly available on the market can be used as is. Since a water dispersant is generally mixed, the indigo powder is washed with hot water and then dried to remove the dispersant completely. It is thereafter stirred and washed in concentrated hydrochloric acid, preferably, in concentrated hydrochloric acid having a concentration of 35% or higher and is then dewatered completely for use. By this purification treatment, impurities such as the above-mentioned indirubin and indoxyl red are converted into their hydrochlorides and are hence extracted into the water layer. The treatment of indigo with hydrochloric acid cannot bring about any significant effects if diluted hydrochloric acid is used as the hydrochloric acid. Sulfuric acid cannot be used in place of hydrochloric acid, because the sulfonated derivative of indigo is formed.

Indigo is used in an amount of 0.01–1.0 wt. %, preferably, 0.05–0.3 wt. % based on the polymer. Any amounts smaller than 0.01% are too little to show sufficient coloring effects. On the other hand, the use of indigo at high concentrations in excess of 1.0% results in the formation of filaments having slightly lowered strength when spun.

As a method for adding indigo to a pelletized polymer, indigo may be mixed directly with the polymer without any solvent or a master batch may be prepared directly without any solvent. When indigo is mixed directly as mentioned above, the indigo dye is however lost upon its mixing with the polymer for coloring the latter. In addition, the tinting power is not fully sufficient. In the process of this invention, it is hence desirable to prepare a dispersion by using a non-aqueous organic solvent and then to color the polymer.

According to the process of this invention, it is preferable to prepare a high-concentration dispersion of indigo by using a non-aqueous solvent such as toluene, xylene or hexane. A small portion of the polymer is then added to the dispersion to prepare a master batch of a high concentration. The master batch is then diluted with the polymer prior to its use.

It is preferable that the solvent, which serves as a dispersant for indigo, does not dissolve polymers at all and has a low boiling point. If a solvent capable of dissolving a polymer to be used, difficulties are encountered upon removal of the solvent. Therefore, DMSO, DMF and the like are not suitable for the process of this invention because they dissolve polymers.

For coloring polyglycolic acid, ethyl acetate is particularly preferred. In the case of polylactic acid, hexane is preferred.

In this invention, a polymer desired for the preparation of a master batch is added to the above-described indigo dispersion. The resultant mixture is then heated to remove the solvent almost completely, whereby a high-concentration master batch with indigo adhered on the polymer is prepared in advance. Upon preparation of the master batch, indigo is added and mixed completely in such an amount that in the case of sutures, the concentration of indigo becomes 5–10 times (preferably, 0.05–5.0 wt. %) the indigo concentration upon spinning (preferably, 0.01–1.0 wt. %). While heating the resultant mixture at 50°–70° C., a majority of the solvent is removed under reduced pressure to obtain a wet master batch. The wet master batch is then heated up to 120° C. or lower, at which the master batch is heated under a reduced pressure of 20 mmHg or so for several hours, for example, for about 3 hours, so that a dry master batch containing 0.1% or less of the solvent is obtained. Here, it is necessary to effect the deaeration at temperatures below 120° C. Since many hours are required for the deaeration, the polymer is subjected to thermal deterioration in the course of its deaeration at temperatures higher than 120° C.

The thus-obtained master batch is kneaded with a fresh supply of the uncolored polymer by a method known per se in the art, thereby obtaining a blue-colored polymer.

Upon mixing the master batch with the uncolored polymer, it is preferable to mix 5–10 parts by weight of the uncolored polymer per part by weight of the master batch. As a result, the concentration of indigo dispersed in the thus-colored polymer ranges from 0.01 wt. % to 1.0 wt. %.

When spinning the thus-obtained blue-colored polymer in order to obtain sutures by way of example, the blue-colored polymer is melt-spun through a spinneret having 8–40 fine holes by means of a usual melt extruder so as to produce multifilaments. The extrusion is conducted at 10–200 kg/cm$^2$ and 230°–250° C. The extrusion pressure is produced by the extrusion screw.

After the spinning, the multifilaments are continuously fed onto a hot plate maintained at 120° C., where they are stretched about fourfold to obtain blue-colored good multifilaments having a tensile strength of 6.5 g/denier. The multifilaments are then braided and after sterilization in a manner known per se in the art, are sealed ready for use as surgical sutures.

Certain examples of this invention will be described hereinafter. In the following Examples, the indigo contents were analyzed in the following manner.

Quantitative analysis of indigo

One gram of each dyed polymer or spun and stretched fibers was boiled for 10 minutes in 20 ml of dimethylformamide. After cooling the mixture to 50° C. or lower, it was filtered. The resulting solution was diluted as needed and the intensity of an absorption peak at 610 nm was measured by a visible light spectrophotometer. The content was then calculated.

EXAMPLE 1

Twenty grams of glycolite (m.p. 83.5°–84.5° C.) obtained from oxyacetic acid (glycolic acid) were charged in a thick-walled cylindrical polymerization vessel made of stainless steel (separable type: the main body and cover are separable), followed by addition of 0.3 ml of a chloroform solution containing 0.6 mg of stannous octate (0.003 wt. %, $1.5 \times 10^{-6}$ mole) and 0.3 ml of another chloroform solution containing 48.0 mg of lauryl alcohol (0.24 wt. %, $2.6 \times 10^{-4}$ mole; 80 times by weight the amount of the stannous octate catalyst). After deaerating the resultant mixture for 2 hours in vacuo (1–5 mmHg), the polymerization vessel was purged with nitrogen gas. The mixture was then heated and polymerized for 2–6 hours at 200°–230° C. in a nitrogen gas atmosphere by means of a mantle heater. After completion of the polymerization, the polymerization mixture was drawn out, as was, of the polymerization vessel from a lower part of the vessel and was then fed to a pelletizer. Upon its pelletization, 19 g of colorless polyglycolic acid was obtained. The viscosity of the polyglycolic acid was measured. Its intrinsic viscosity was 1.06 ($[\eta]_{inh}=1.06$). Its melting index was 2.0 (MI=2.0).

To 200 g of the above-prepared pellets of polyglycolic acid, a liquid preparation of 1.0 g of indigo powder dispersed and mixed in 200 ml of ethyl acetate was added. After mixing them thoroughly, the resultant mixture was deaerated at 50°–55° C. in vacuo until the ethyl acetate solvent was removed substantially to 0.1% or less. Thus, a master batch containing 0.5% of indigo was prepared.

After thoroughly mixing 100 g of the master batch with 900 g of polyglycolic acid, the resultant mixture was dried at 120° C. for 3 hours under reduced pressure of 20 mmHg to obtain 1 kg of blue-colored polyglycolic acid.

Pellets of the blue-colored polyglycolic acid were spun at 245° C. by a conventional melt-spinning machine. The resultant multifilaments were then stretched fourfold on a hot plate of 120° C., thereby obtaining blue-colored good filaments which had a tensile strength of 6.5 g/denier and were suitable for use in the production of sutures. $[\eta]=0.90$.

Indigo was contained in an amount of 0.05% in the thus-obtained blue-colored filaments. It was hence confirmed that the indigo, which had been used, was contained in its entirety in the polymer.

EXAMPLE 2

Two hundred grams of a master batch, which had been obtained in exactly the same manner as in Example 1 except for the use of 1.5 g of the indigo powder and had an indigo content of 0.75%, and 800 g of polyglycolic acid were mixed together to obtain 1 kg of a blue-colored polyglycolic acid.

The blue-colored polyglycolic acid was then spun and stretched in the same manner as in Example 1, thereby obtaining blue-colored filaments which had an indigo content of 0.15%.

EXAMPLE 3

In the same manner as in Example 1 except that l-lactide was employed in place of the raw material glycolite, pellets of poly(l-lactic acid) were obtained. $[\eta]=1.4$.

To 100 g of the pellets, 1.5 g of indigo powder was mixed directly to prepare a master batch having an indigo content of about 1.5%. One hundred grams of the master batch were mixed with 900 g of the pellets, thereby obtaining blue-colored pellets the theoretical indigo content of which was 0.15%.

The blue-colored pellets were then spun in the same manner as in Example 1. The indigo content of the resulting filaments was 0.13%.

EXAMPLE 4

Twenty grams of indigo powder ("INDIGOPURE EX", trade name; product of Mitsui-Toatsu Dyes Inc.), which had been washed with hot water and then dried, were added to 100 ml of 35% hydrochloric acid. The resultant mixture was stirred at room temperature for 30 minutes. It was then filtered under reduced pressure through a suction funnel equipped with a glass filter. The filtrate was washed with distilled water until the pH of the washing becomes 6 or higher.

The thus-obtained cake was dried and ground to obtain 19.4 g of purified indigo.

In 200 ml of ethyl acetate, 1.0 g of the aboveobtained purified indigo powder was mixed and dispersed, followed by a further addition of 200 g of the pellets of polyglycolic acid obtained in Example 1. After mixing them thoroughly, the resultant mixture was deaerated at 50°–55° C. in vacuo. The resulting wet master batch was then heated to 120° C. in vacuo to remove the ethyl acetate solvent substantially to 0.1% or less, thereby preparing a master batch with 0.5% of indigo incorporated therein.

After thoroughly mixing and kneading 100 g of the master batch with 900 g of the polyglycolic acid, the resulting mixture was dried at 120° C. under a reduced pressure of 20 mmHg for 3 hours to obtain 1 kg of colored polyglycolic acid.

Pellets of the colored polyglycolic acid were spun at 245° C. by a conventional melt-spinning machine. The resultant multifilaments were then stretched fourfold on a hot plate of 120° C., thereby obtaining blue-colored good filaments which had a tensile strength of 6.5 g/denier and were suitable for use in the production of sutures. $[\eta]=0.90$.

Indigo was contained in an amount of 0.05% in the thus-obtained blue-colored filaments. It was hence confirmed that the indigo, which had been used, was contained in its entirety in the polymer.

We claim:

1. Blue-colored bioabsorbable surgical fibers made of a polymer obtained by coloring a bioabsorbable polymer, which is processed by adding and dispersing a bioabsorbable polymer, selected from the group consisting of polyglycolic acid and glycolic acid-l-lactic acid copolymers each of which is useful as a surgical fiber, and indigo, which has been purified with at least 35 wt. % hydrochloric acid, in a non-aqueous organic solvent having low solubility for the polymer and indigo, heating the resultant dispersion at a temperature below 120° C. to distill off the solvent, thereby obtaining a master batch with the indigo incorporated therein at a high concentration, mixing and kneading the master batch with a fresh supply of the polymer, and then spinning the resultant polymer mixture.

2. The fibers as claimed in claim 1, wherein the indigo is contained in an amount of 0.01–1.0 wt. % of the polymer.

* * * * *